US012727915B2

(12) United States Patent
Boyes et al.

(10) Patent No.: US 12,727,915 B2
(45) Date of Patent: Sep. 8, 2026

(54) ACCESSORY FOR ARRANGING A SURGICAL INSTRUMENT WITHIN A CANNULA SHAFT

(71) Applicant: Fisher & Paykel Healthcare Limited, Auckland (NZ)

(72) Inventors: Richard John Boyes, Auckland (NZ); Zach Jonathan Warner, Auckland (NZ); Benjamin Elliot Hardinge Pegman, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 10 days.

(21) Appl. No.: 18/682,095

(22) PCT Filed: Aug. 16, 2022

(86) PCT No.: PCT/IB2022/057641

§ 371 (c)(1),
(2) Date: Feb. 7, 2024

(87) PCT Pub. No.: WO2023/021408

PCT Pub. Date: Feb. 23, 2023

(65) Prior Publication Data

US 2025/0195106 A1 Jun. 19, 2025

Related U.S. Application Data

(60) Provisional application No. 63/260,296, filed on Aug. 16, 2021.

(51) Int. Cl.

| | |
|---|---|
| ***A61B 1/12*** | (2006.01) |
| ***A61B 17/34*** | (2006.01) |

(52) U.S. Cl.

CPC .......... *A61B 17/3474* (2013.01); *A61B 1/127* (2013.01); *A61B 17/3468* (2013.01)

(58) Field of Classification Search

CPC .. A61M 13/003; A61B 17/3421; A61B 1/015; A61B 17/3474; A61B 1/127; A61B 17/3468; A61B 1/00135

See application file for complete search history.

(56) References Cited

U.S. PATENT DOCUMENTS

| | | | |
|---|---|---|---|
| 4,211,229 | A | 7/1980 | Wurster |
| 4,497,550 | A | 2/1985 | Ouchi et al. |

(Continued)

FOREIGN PATENT DOCUMENTS

| | | | | |
|---|---|---|---|---|
| CN | 117122391 A | * 11/2023 | | A61B 17/3403 |
| GB | 2628817 A | * 10/2024 | | A61B 1/126 |

(Continued)

OTHER PUBLICATIONS

International Search Report and Written Opinion dated Nov. 18, 2022 for PCT International Application No. PCT/IB2022/057641.

*Primary Examiner* — Jacqueline T Johanas
(74) *Attorney, Agent, or Firm* — EIP US LLP

(57) ABSTRACT

Accessory 10 for arranging a surgical instrument 12 within a cannula shaft 14. The accessory 10 includes a body 11 defining a bore 16 configured to receive and position the instrument 12, such that arranging the instrument 12 within the bore 16 defines at least one first flow path 18 between the body and the instrument 12. The body 11 is configured to fit within and position relative to the cannula shaft 14, such that arranging the body 11 within the cannula shaft 14 defines at least one second flow path 20 between the body 11 and the cannula shaft 14. The body 11 is further configured to allow fluid to flow through the cannula shaft 14 and past the instrument 12 via one or more of the at least one first flow path 18 and the at least one second flow path 20.

16 Claims, 11 Drawing Sheets

(56) References Cited

U.S. PATENT DOCUMENTS 5,167,220 A 12/1992 Brown
5,312,332 A * 5/1994 Bales ............... A61B 17/00234 604/28
5,313,934 A 5/1994 Wiita et al.
6,126,592 A 10/2000 Proch et al.
7,854,724 B2 * 12/2010 Stearns ............. A61B 17/3474 604/23
8,047,215 B1 11/2011 Sasaki
8,096,944 B2 1/2012 Harrel
9,161,680 B2 * 10/2015 Bellofatto ............ A61B 1/0011
10,398,494 B2 * 9/2019 Carter ................ A61B 17/3421
10,549,041 B2 * 2/2020 Fech .................. A61M 5/3007
10,595,919 B2 * 3/2020 Haufe ................ A61B 17/3472
2004/0204671 A1 * 10/2004 Stubbs .............. A61B 17/3423 604/164.01
2007/0213675 A1 9/2007 Albrecht et al.
2012/0165610 A1 * 6/2012 Poll .................... A61B 17/3421 600/157
2014/0088491 A1 * 3/2014 Azarbarzin ............ A61B 34/30 604/26
2014/0100567 A1 * 4/2014 Edwards .......... A61B 17/32002 606/45
2014/0371667 A1 12/2014 Kasuya
2014/0371763 A1 * 12/2014 Poll ........................ A61B 34/30 606/130
2015/0087907 A1 3/2015 Konstorum et al.
2015/0148608 A1 * 5/2015 Fukushima ........ A61B 1/00094 600/116
2016/0089006 A1 3/2016 Poll et al.
2016/0278623 A1 9/2016 Hirata
2017/0196439 A1 7/2017 Dejima
2020/0022726 A1 1/2020 Mikol et al.
2021/0236749 A1 8/2021 Kokhanenko et al.
2021/0338278 A1 * 11/2021 Scott .................. A61M 13/003
2023/0082376 A1 * 3/2023 Warner ............. A61B 1/00091 600/206
2023/0157520 A1 * 5/2023 Jensrud ............. A61B 1/00068 600/133

FOREIGN PATENT DOCUMENTS

WO WO-9902112 A1 * 1/1999 ............... A61F 7/12
WO 2010037099 A1 4/2010
WO 2018015567 A2 1/2018
WO WO-2020036497 A1 * 2/2020 ......... A61B 17/3474
WO WO-2020036498 A1 * 2/2020 ......... A61B 17/3474
WO 2021161231 A1 8/2021
WO WO-2024134602 A1 * 6/2024 ......... A61B 17/3474

* cited by examiner

ACCESSORY FOR ARRANGING A SURGICAL INSTRUMENT WITHIN A CANNULA SHAFT

TECHNICAL FIELD

The present disclosure relates, generally, to accessories for surgical instruments and, particularly, to such accessories configured to position an instrument within a shaft of a cannula.

BACKGROUND

Various medical procedures require inserting an instrument into a body cavity through an opening, such as an incision, arranged to allow access into the cavity. Such procedures may include, or be referred to generally, as closed-type medical procedures. A cannula can be inserted into the opening and the instrument can access the cavity through the cannula. For example, in endoscopic procedures a medical practitioner may insert an endoscope, or other imaging device, through the cannula to allow capturing an image (including video footage) of the body cavity. In laparoscopic procedures, a medical practitioner may insert a medical instrument, such as a laparoscope or an electrocautery device, through the cannula to perform a medical procedure in the body cavity. Similar approaches are used in a range of closed-type procedures, such as thoracoscopy, gastroscopy, and bronchoscopy.

Many closed-type procedures involve surgical gases, such as carbon dioxide or air, being conveyed to the body cavity. For example, an insufflator connected to a gas source can deliver gas to the body cavity to inflate the body cavity and/or resist collapse of the body cavity during the procedure. Where a cannula is used in the procedure, the gases may be conveyed to a gas inlet port of the cannula and through the cannula into the cavity.

When an instrument, such as an endoscope or laparoscope (commonly referred to as a 'scope') is inserted through a cannula and into a body cavity, the relative temperature difference between the instrument and the cavity, and/or humidity within the cavity, can cause condensation to form on the instrument. When condensation forms on a viewing portion of the instrument, typically being a lens, this can interfere with imaging the body cavity. Furthermore, when operating a scope within the body, bodily fluids, tissue, debris and/or smoke can also negatively affect image quality.

Any discussion of documents, acts, materials, devices, articles or the like which has been included in the present specification is not to be taken as an admission that any or all of these matters were common general knowledge in the field relevant to the present disclosure as it existed before the priority date of each of the appended claims.

SUMMARY

Condensation may occur when the temperature of a gas falls below the dew point temperature for the level of humidity the gas is carrying, and/or if there are surfaces below the dew-point temperature. The human body is a warm and humid environment, having an internal temperature of about 37° C. When cold (for example, at or below typical room temperature, and/or below a typical human body temperature) cameras, scopes, or other medical instruments are inserted into this environment, condensation can cause droplets to form on the viewing portion, such as the lens, or elsewhere on the scope, which can drip onto the lens area. Similarly, condensation can form droplets on an internal wall of a cannula, which may drip down, such as for example, onto a viewing portion, such as the lens area. When such fluid collects on the lens area, this inhibits light transmission through the lens, consequently impairing vision of the operator of the scope. It will be appreciated that the terms "viewing portion", "lens area" and "lens" may be used interchangeably throughout this specification, and that each refer to a distal portion of a surgical instrument configured for facilitating remote vision for an operator.

Vision through a viewing portion of a surgical instrument can also be impaired by other factors, such as when contaminants, for example, smoke and the like, are deposited on the viewing portion and/or are within the field of view. During a medical procedure, moving or operating a scope can cause various other materials to be arranged in front of the lens of the scope to inhibit light transmission through the lens. For example, the lens may be positioned adjacent or against bodily fluids, tissue, debris, or particles created by the procedure, such as surgical smoke. Any such materials or debris located proximal to or on the lens can impede vision, for example, of a surgeon or other medical personnel participating in the medical procedure. When vision through the lens becomes limited due to the presence of particles, fluid droplets, or the like, it may be necessary to remove the scope and/or the other medical instruments and wipe it (or them) down to remove the contamination. However, removing a medical instrument from the surgical cavity can cause it to cool to below the patient's body temperature. As a result, when the instrument is reinserted, further condensation can form which, again, can inhibit operator vision. Past approaches to resolve this include pre-warming the medical instruments, and/or using a light or a heating source at the end of the scope to warm the lens. Such interventions typically require additional steps that can negatively impact the workflow and efficiency of the procedure. Furthermore, repetitive heating of instruments, or parts thereof, such as with a heating element adjacent a lens, can affect the structure of the instrument, and/or increase complexity of sterilizing the instrument.

According to one disclosed aspect, there is provided an accessory for arranging a surgical instrument within a cannula shaft. The accessory includes a body defining a bore configured to receive and position the instrument such that arranging the instrument within the bore defines at least one first flow path between the body and the instrument, and the body being configured to fit within and position relative to the cannula shaft such that arranging the body within the cannula shaft defines at least one second flow path between the body and the cannula shaft. The body is configured to allow fluid to flow through the cannula shaft and past the instrument via one or more of the at least one first flow path and the at least one second flow path.

The accessory may be embodied in various forms suitable for receiving and positioning the surgical instrument. This includes embodying the accessory as any of a sheath, sleeve, housing, casing, or adaptor for the instrument.

The bore may define an internal diameter configured to position the body on, or close to, the instrument in at least two locations, and the body may define an external diameter configured to position the body in the cannula shaft in at least two locations, The body may be shaped to tangentially abut at least one of the instrument and the cannula shaft in the at least two locations.

The bore may be shaped to extend at least partially along the instrument in at least two locations to allow defining at least two first flow paths, and define an external region shaped to extend at least partially along the cannula shaft in at least two locations to allow defining at least two second flow paths.

The body may define a plurality of internal projections extending into the bore and configured to positon the body relative to the instrument, and define a plurality of external projections extending away from the bore and configured to position the body relative to the cannula shaft.

At least one of the internal projections and the external projections may be arranged in an annular array to be evenly spaced about the bore.

At least some of the internal projections may be arranged in opposed pairs to position the body at opposed sides of the instrument. Additionally or alternatively, at least some of the external projections may be arranged in opposed pairs to position the body at opposed sides of the cannula shaft.

One or more of the projections may be in the form of longitudinally extending ribs.

The body may have a cross-sectional profile defining an array of hollow projections extending radially outwards from the bore, and at least some of the hollow projections be dimensioned to position the body in the cannula shaft.

The array may include at least one pair of hollow lobes dimensioned to position the body at opposed sides of the cannula shaft.

The body may be shaped to position at least one of: the instrument coaxially to the bore; the instrument coaxially to the cannula shaft; and itself coaxially to the cannula shaft.

The body may be shaped to slidingly engage at least one of the instrument and the cannula shaft.

The accessory may also include a distal portion having the body, a proximal portion dimensioned to fit within the cannula shaft, and an intermediate portion interposed between the distal portion and the proximal portion. The intermediate portion may be configured to seal against the cannula shaft. The proximal portion may define at least one aperture arranged to allow fluid to flow into the bore and along the at least one first flow path.

The distal portion and the body may be integrally formed. The body may be separate from, and configured for connection to, the distal portion.

The proximal portion may define the at least one aperture adjacent the intermediate portion.

The proximal portion may define a tapered region extending away from the intermediate portion. In such embodiments, the at least one aperture may be defined in the tapered region.

The proximal portion may define an annular array of the apertures.

The at least one aperture may be associated with at least one one-way valve to control fluid flow through the at least one aperture.

The body may include a positioning portion defining a proximal end, and the proximal end is spaced axially from the intermediate portion. In such embodiments, the proximal end of the positioning portion may be spaced from the intermediate portion by a distance equal to, or less than, a longitudinal length of the cannula shaft.

Where the cannula shaft is associated with an instrument seal, the proximal end of the positioning portion may be spaced from the intermediate portion by a distance equal to, or less than, a longitudinal length between a distal end of the cannula shaft and the instrument seal.

The intermediate portion may be configured to frictionally engage the cannula shaft to seal against the shaft. The intermediate portion may carry at least one resiliently deformable first seal configured to seal against the cannula shaft.

The proximal portion may be configured to seal against the instrument at a location spaced proximally from the at least one aperture. The proximal portion may carry at least one resiliently deformable second seal configured to seal against the instrument.

According to another disclosed aspect, there is provided a sheath for arranging a surgical instrument in a cannula shaft. The sheath includes a body dimensioned to fit within the cannula shaft, the body defining a bore to receive the instrument, the body having a proximal portion and a distal portion, the distal portion having an open distal end, and a seal interposed between the proximal portion and the distal portion, the seal configured to seal against the cannula shaft. The proximal portion defines at least one aperture to allow fluid to flow from the cannula shaft and through the bore to exit from the open distal end.

The distal portion may be shaped to slidingly engage the instrument and allow the fluid to flow axially to pass the instrument. Additionally or alternatively, the distal portion may be shaped to slidingly engage the cannula shaft and allow the fluid to flow axially through the cannula shaft to pass the distal portion.

According to another disclosed aspect, there is provided a system for delivering gases to a surgical site. The system includes a gas source, a cannula having a shaft in fluid communication with the gas source, a surgical instrument, and an accessory having a first positioning portion configured to receive and position the instrument, the first positioning portion shaped to allow fluid to flow axially through the cannula shaft and alongside the accessory, and having a second positioning portion configured to be received in, and positioned relative to, the cannula shaft, the second positioning portion shaped to allow fluid to flow axially between the cannula shaft and the accessory. The accessory defines at least one aperture to allow fluid to flow into the first positioning portion to bypass the instrument, and has a sealing portion arranged operatively downstream of the at least one aperture and configured to seal against the cannula shaft to allow directing fluid to flow through the at least one aperture.

According to a further disclosed aspect, there is provided a method for delivery gases to a surgical site. The method includes inserting a surgical instrument into a sheath to define at least one first flow path between the sheath and the instrument, inserting the sheath into the cannula shaft to define at least one second flow path between the sheath and the cannula shaft, and conveying gases through one or more of the at least one first flow path and the at least one second flow path to exit into the surgical site.

Inserting the sheath into the cannula shaft may include inserting the sheath a defined distance into the cannula shaft. Inserting the sheath a first distance may cause the gases to flow through the at least one second flow path. Inserting the sheath a second distance, being greater than the first distance, may cause the gases to flow through the at least one first flow path. Inserting the sheath a third distance, being greater than the first distance and less than the second distance, may cause the gases to flow through at least one of the at least one second flow path and the at least one first flow path.

According to another disclosed aspect, there is provided a system for delivering gases to a surgical site. The system includes a gas source, a cannula having a shaft in fluid communication with the gas source via a gas inlet port, and having a housing seal, a surgical instrument, and an accessory defining a proximal end, a distal end, and a bore between the ends configured to receive the instrument, the accessory configured to fit within the cannula shaft to at least partially define at least two flow paths to allow gas to flow axially through the cannula shaft and past the instrument. Arranging the accessory at a first insertion position relative to the cannula shaft causes gas to flow through a first flow path defined between the accessory and the cannula shaft. Arranging the accessory at a second insertion position relative to the cannula shaft causes gas to flow through a second flow path defined between the accessory and the instrument.

The accessory may be further configured such that arranging the accessory at a third insertion position relative to the cannula shaft causes gas to flow through the first flow path and the second flow path.

The accessory may define at least one aperture arranged to allow fluid to flow into the bore. At the first insertion position, the at least one aperture may be arranged at, or spaced proximally from, the housing seal to inhibit gas from entering the at least one aperture and through the second flow path. At the second insertion position, the at least one aperture may be spaced distally from the housing seal and within the cannula shaft to allow gas to enter the at least one aperture and through the second flow path, and inhibit gas flowing through the first flow path. At the third insertion position, the at least one aperture may be spaced between the housing seal and the cannula shaft to allow gas to flow through the first flow path and the second flow path.

The at least one aperture may be associated with one or more aperture seals to restrict gas flow to a single direction through the at least one aperture.

The accessory may include one or more shaft seals configured to seal against the cannula shaft, the one or more shaft seals being spaced distally from the at least one aperture.

The instrument may be a scope, and the accessory may be configured to cause gas to flow concentrically to the scope.

At the first insertion position, the accessory may be configured to direct gas to exit from the cannula shaft. At the second insertion position, the accessory may be configured to direct gas to exit from its distal end. At the third insertion position, the accessory may be configured to direct gas to exit from its distal end and from the cannula shaft.

The scope may include a lens, and the accessory may be configured to cause gas to flow past the lens.

According to a further disclosed aspect, there is provided a sheath for a surgical instrument, where the sheath includes a body defining an open distal end and a passage configured to receive the instrument. The body has an internal region configured to direct fluid flow axially through the passage to pass an instrument arranged within the passage. The body has an external region configured to direct fluid flow axially adjacent the sheath to pass the sheath and an instrument arranged within the passage.

The internal region may include a plurality of internal projections extending into the passage and arranged to position the instrument, and the external region include a plurality of external projections extending away from the passage.

At least one of the plurality of internal projections and the plurality of external projections are arranged in an annular array to be evenly spaced about the passage.

At least some of the internal projections may be arranged in opposed pairs to position the body at opposed sides of the instrument.

At least one of the internal projections and the external projections may include longitudinally extending ribs.

At least a portion of the body may have a cross-sectional profile defining an array of hollow projections extending radially outwards from the passage. The array may include at least one pair of hollow lobes. Each lobe may define a curved outer surface for positioning the body in a shaft. Each lobe may be joined by a curved portion of the cross-sectional profile configured to receive the instrument.

According to a further aspects of the disclosure, there is provided a sheath for a surgical instrument, where the sheath includes a body defining an open distal end and a passage dimensioned to receive the surgical instrument. The body has an external region defining an outer positioning portion configured to be coincident to an outer notional circle in at least one location, and has an internal region defining an inner positioning portion configured to be coincident to an inner notional circle in at least one location.

At least one of the inner positioning portion and the outer positioning portion may be configured to be tangential to the respective notional circle at two or more points.

At least one of the inner positioning portion and the outer positioning portion may be configured to be extend at least partially about the respective notional circle.

The body may define opposed ends and a longitudinal axis extending between the ends and through the bore, and at least one of the inner positioning portion and the outer positioning portion may extend only partially along the longitudinal axis. The inner positioning portion may extend along a first portion of the longitudinal axis, and the outer positioning portion extend along a second portion of the longitudinal axis, and the first portion and the second portion may be substantially axially aligned.

The sheath may include a distal portion having the body, a proximal portion, and an intermediate portion interposed between the distal portion and the proximal portion. In such embodiments, the intermediate portion may be configured to seal against a shaft, and the proximal portion define at least one aperture arranged to allow fluid to flow into the passage and exit from the open distal end.

The distal portion and the body may be integrally formed.

The proximal portion may define the at least one aperture adjacent the intermediate portion.

The proximal portion may define a tapered region extending away from the intermediate portion. The at least one aperture may be defined in the tapered region.

The proximal portion may define an annular array of the apertures. The at least one aperture may be associated with at least one one-way valve to control fluid flow through the at least one aperture.

The body may include a positioning portion defining a proximal end, and the proximal end may be spaced axially from the intermediate portion.

The intermediate portion may be configured to frictionally engage a shaft. The intermediate portion may carry a resiliently deformable first seal configured to seal against a shaft. The proximal portion may be configured to seal against the instrument at a location spaced proximally from the at least one aperture. The proximal portion may carry a resiliently deformable second seal configured to seal against the instrument.

According to other disclosed aspects, there is provided an assembly for positioning a surgical instrument, the assembly including a cannula having an elongate shaft defining an open distal end, and the sheath as described in any of the preceding paragraphs, where the external region of the sheath is configured to fit within the shaft of the cannula.

The cannula may have a proximal portion, referred to as the cannula body, including a gas inlet port. The elongate shaft may have an internal sidewall which defines a lumen. The lumen may be configured to provide gasses, such as insufflation gases, to a surgical cavity. The lumen may be in fluid communication between a gases inlet and an outlet proximate a distal end of the cannula shaft.

The cannula may include a gas inlet port spaced from the distal end of the shaft, and the port be in fluid communication with the shaft. The assembly may also include a tube configured to couple with the gas inlet port to allow conveying gases to the gas inlet port.

The tube may be associated with a heating element operable to heat gas contained within the tube. The assembly may also include a filter configured to be arranged across the tube to allow filtering gas conveyed through the tube. The filter may be associated with a heating element operable to heat gas passing through the filter.

The assembly may also include a humidifier configured to couple to a gas source and operable to humidify gas received from the gas source. The humidifier may be configured to couple with a tube to allow conveying humidified gas to the tube. The assembly may include a further tube configured to couple the humidifier with the gas source.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated embodiments may comprise steps, features and/or integers disclosed herein or indicated in the specification of this application individually or collectively, and any and all combinations of two or more of said steps or features.

BRIEF DESCRIPTION OF DRAWINGS

Embodiments will now be described by way of example only with reference to the accompany drawings in which.

DESCRIPTION OF EMBODIMENTS

Figure 1:
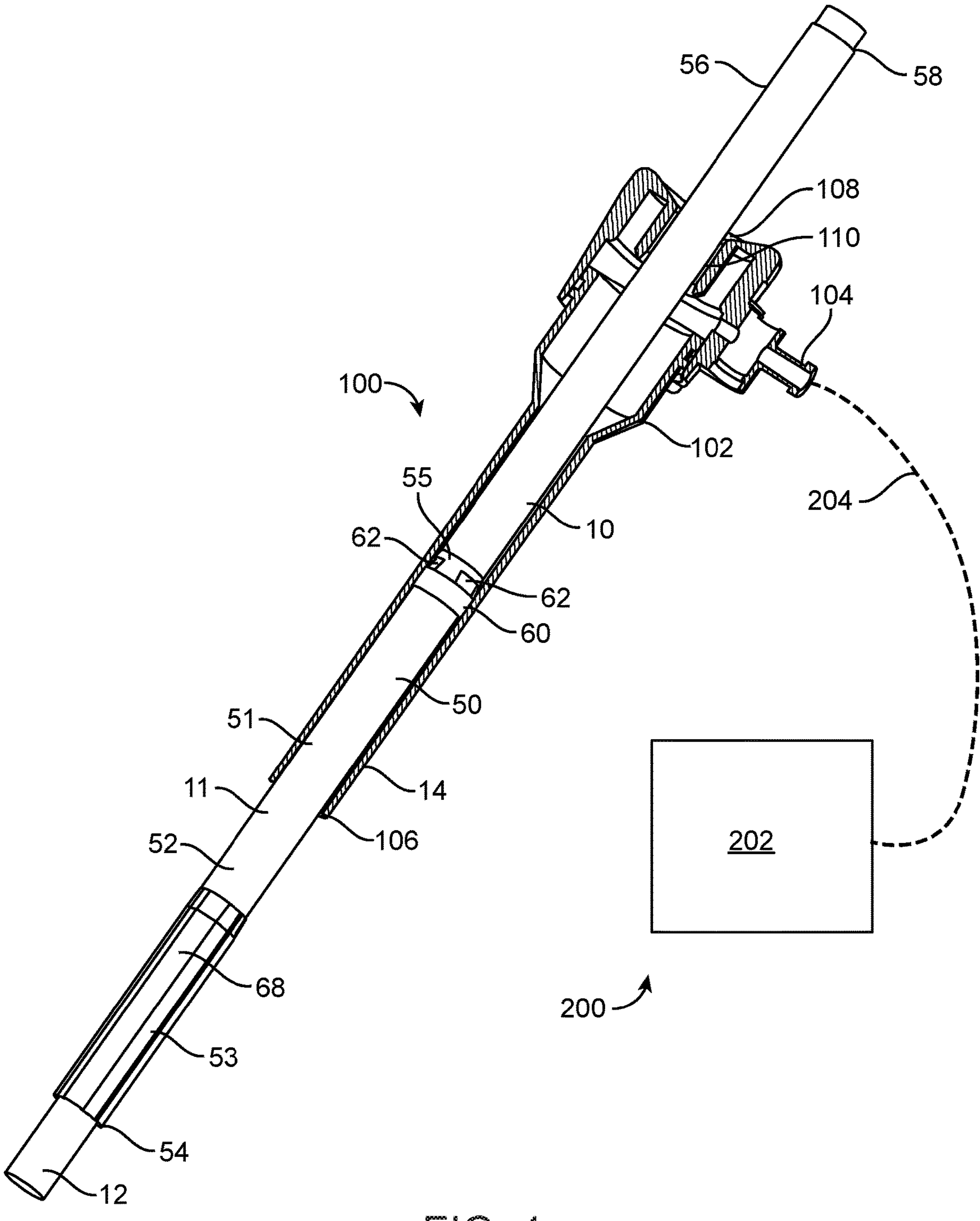
FIG. 1 is a partial section, perspective view of a system for use in surgical procedures.

In the drawings, reference numeral 10 generally designates an accessory 10 for arranging a surgical instrument 12 within a cannula shaft 14. The accessory 10 includes a body 11 defining a bore 16, being a passage, or sometimes referred to as a lumen, configured to receive and position the instrument 12, such that arranging the instrument 12 within the bore 16 defines at least one first flow path 18 between the body and the instrument 12. The body 11 is configured to fit within and position relative to the cannula shaft 14 such that arranging the body 11 within the cannula shaft 14 defines at least one second flow path 20 between the body 11 and the cannula shaft 14. The body 11 is further configured to allow fluid to flow through the cannula shaft 14 and past the instrument 12 via one or more of the at least one first flow path 18 and the at least one second flow path 20.

Throughout this disclosure, "proximal" and "distal" are used to indicate relative position of components. It will be appreciated that these terms are used in accordance with the conventional meaning in the art, where "proximal" refers to being located proximally, towards, or near to the user, and "distal" refers to being located distally, spaced, or away from the user. In the context of this disclosure, the user is typically an operator of the instrument 12, such as a surgeon or other medical practitioner.

FIG. 1 shows a first embodiment 50 of the accessory 10 arranged as part of an assembly 100 for use during a surgical, or other medical, procedure. The assembly 100 includes a cannula 102 having the shaft 14, the accessory 50, and the instrument 12. In the illustrated assembly 100, the instrument 12 is in the form of a scope, such as an endoscope or laparoscope. In other embodiments (not illustrated), the instrument 12 comprises any of an electrocautery device, a tool for electro-surgery, energy or laser cutting, and/or cauterizing, or other elongate instrument.

The assembly 100 is shown in FIG. 1 as part of a system 200 for delivering gases to a body cavity, such as during a surgical procedure. It will be appreciated that the body cavity may be a naturally occurring cavity defined by the body and/or a cavity at least partially formed at a surgical site by intervention during the surgical procedure. The system 200 includes the assembly 100 and a gas source 202 to allow conveying one or more gases to the cannula 102. The gas source 202 may be static, such as a tank of pressurised gas, or include a gas delivery mechanism, such as an insufflator (not illustrated), to pressurise gas received from the gas source 202. It will be appreciated that, in other embodiments (not illustrated), the gas source 202 may be substituted with a fluid source to allow delivering one or more fluids to the assembly 100. In some embodiments, a medicament may be supplied with the gas or fluid conveyed to the assembly 100.

In some embodiments of the system 200, a humidifier (not illustrated) may be located between the gas source 202 and the assembly 100. Various styles or types of humidifiers may be used in combination with other elements of the system 200. Suitable humidifiers may generally comprise an inlet and an outlet, and are configured to hold a volume of humidification fluid, such as water and/or a medicament. The humidifier may comprise a humidifier chamber or medium to hold humidification fluid, and a heater configured to heat at least one of gas and the humidification fluid. The humidifier may be a "pass-over" style humidifier, comprising a heater base or plate, and a chamber.

The gases may be delivered from the gas source 202 to the assembly 100 via one or more delivery tubes or hoses 204. One or more of the tubes 204 may be configured to allow controlling the temperature of the gases as the gases travels between the gas source 202 and the body cavity, such as a surgical cavity. For example, the tube 204 may be associated with a heating element, such as arranged along a length of, or wound around a portion of, the tube 204, to allow heating fluid contained within the tube 204, such as to inhibit condensation forming. In some embodiments (not illustrated), a first tube may deliver gases between the gas source 202 and a humidifier, and a further tube may deliver the gases between the humidifier and the assembly 100.

The one or more tubes 204 may be in fluid communication with one or more filters or filter units (not illustrated). The filter may be arranged across the tube 204 to allow filtering gas conveyed through the tube. For example, a filter may be provided downstream of the gas source 202. Alternatively or additionally, a filter may be provided downstream of the humidifier outlet. In some embodiments, the filter is associated with a heating element which is operable to heat gas passing through the filter.

The cannula 102 has a gas inlet port 104 configured to fluidly couple with the gas source 202, such as via the tube or hose 204, and receive the gas, to be in fluid communication with the gas source 202. The shaft 14 is in fluid communication with the gas inlet port 104, and defines an open distal end 106 from which gas may exit. The cannula 102 has an opposed proximal end 108 having a housing seal 110, or instrument seal, arranged within the housing of the cannula 102 to seal against the instrument 12, or the accessory 10, when arranged within the cannula 102 to inhibit gas leaking from the proximal end 108 of the cannula 102. The cannula 102 is configured to be arranged through an incision or orifice defined in a patient's body to allow access to a body cavity.

Figure 2:
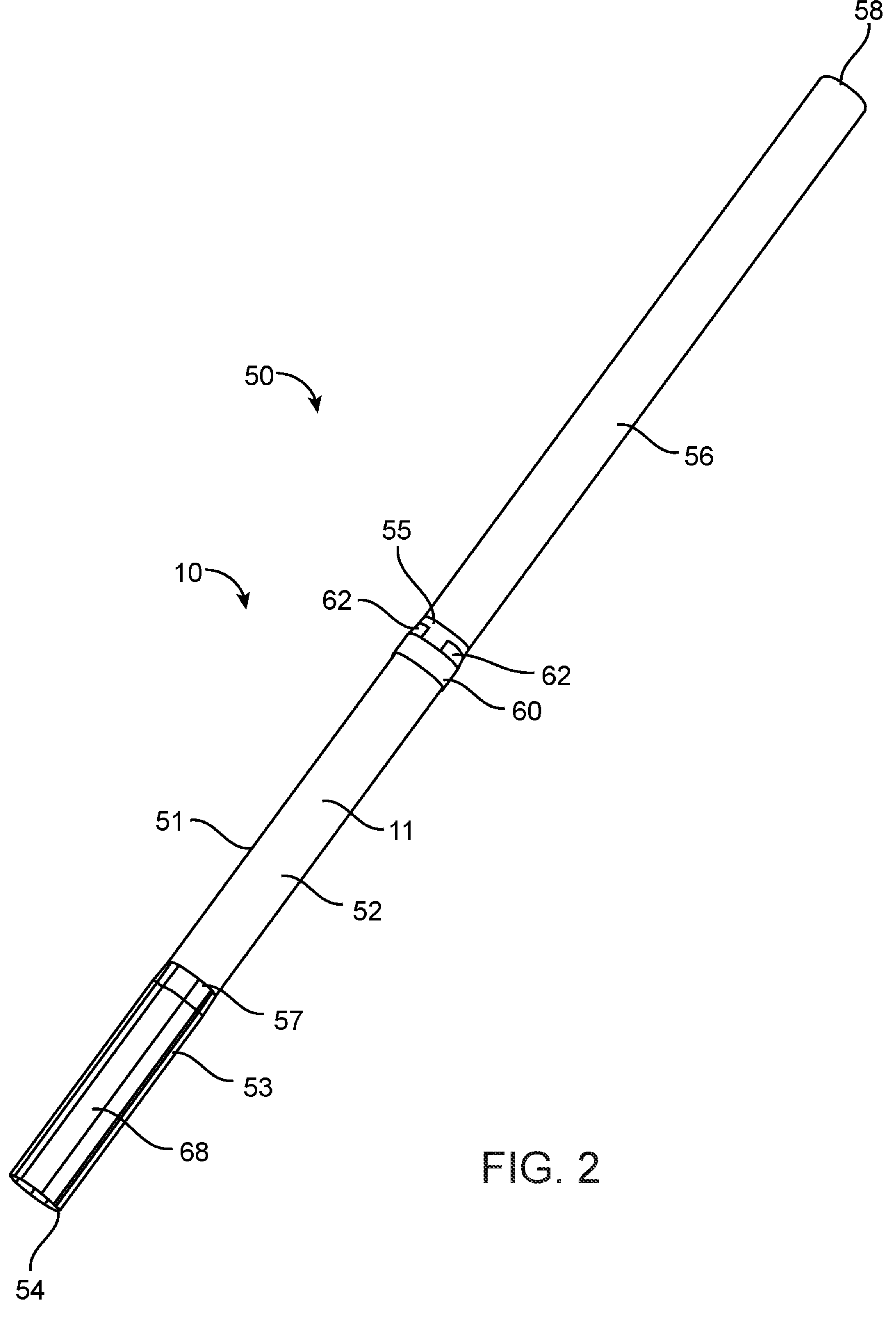
FIG. 2 is a perspective view of a component of the system shown in FIG. 1, being an accessory for a surgical instrument.

FIG. 2 shows the first embodiment of the accessory 50 in isolation. In this disclosure, the accessory 10 may be referred to as a sheath. It will be appreciated that "sheath" is exemplary and is interchangeable with similar labels, such as a sleeve. The accessory 10 may alternatively be referred to as a positioning device.

The accessory 50 has a body 51 which includes a distal portion 52 defining an open distal end 54, a proximal portion 56 defining a proximal end 58, and an intermediate portion 60, or sealing portion, interposed between the distal portion 52 and the proximal portion 56. In the illustrated embodiment 50, the portions 52, 56, 60 of the body 51 are integrally formed to define a unitary body 51. The bore 16 is defined between the distal end 54 and the proximal end 58 such that the proximal end 58 is open to allow receiving the instrument 12 into the bore 16. In other embodiments (not illustrated), at least one or part of the portions 52, 56, 60 is a separate component and joined to the other portion(s) 52, 56, 60 to form the body 51. In some embodiments (not illustrated), the proximal end 58 includes, or is associated with, a mechanism operable such that the bore 16 is selectively openable at the proximal end 28, such as a valve or seal mechanism.

The distal portion 52 and at least a portion of the proximal portion 56 are dimensioned to fit within the cannula shaft 14. The intermediate portion 60 is configured to seal against the cannula shaft 14. In some embodiments, the intermediate portion 60 is dimensioned to frictionally engage the shaft 14. Additionally or alternatively, the intermediate portion 60 carries one or more resiliently deformable seals, such as O-rings or wiper seals, for example, configured to be compressed when arranged within the cannula shaft 14. In some embodiments (not illustrated), part of the proximal portion 56 is flared or otherwise enlarged, or carries a stopper, to inhibit the accessory 50 completely passing through the cannula shaft 14.

The proximal portion 56 defines at least one aperture 62 arranged to allow access into the bore 16. In the illustrated embodiment 50, the proximal portion 56 defines an annular array of the apertures 62 arranged about the bore 16, the array being adjacent the intermediate portion 60 such that the intermediate portion 60 is operatively downstream of the at least one aperture 62 to allow sealing about the body 51 at a downstream position. In other embodiments (not illustrated), the aperture(s) 62 are defined in the proximal portion 56, axially spaced away from the intermediate portion 60.

The distal portion 52 includes a positioning portion 53, being a structure configured, such as being shaped and/or dimensioned so that, in use, as illustrated in FIG. 1, the structure positions the accessory 50 relative to the cannula shaft 14 and/or the instrument 12. The positioning portion 53 may be configured to abut at least one of the cannula shaft 14 and the instrument 12. The positioning portion 53 may be dimensioned to allow clearance between the shaft 14 and instrument 12. The clearance may be defined within a tolerance, for example, less than 0.5 mm. In some embodiments, the positioning portion 53 is configured for sliding engagement with the shaft 14 and/or instrument 12.

In some embodiments (not illustrated), the positioning portion 53 extends from the distal end 54 of the accessory 50, along the distal portion 52, and up to the intermediate portion 60. In other embodiments, the positioning portion 53 extends from the distal end 54 of the accessory 50, along the distal portion 52, and part way towards the intermediate portion 60. In the illustrated embodiment 50, the positioning portion 53 defines a proximal end 57 spaced axially from the intermediate portion 60.

In some embodiments, the proximal end 57 of the positioning portion 53 may be spaced apart from the intermediate portion 60 by a distance less than, or equal to, a longitudinal length of the cannula shaft 14. This can cause either the positioning portion 53 or the intermediate portion 60 to abut the cannula shaft 14 as the accessory 50 is slid through the shaft 14 to cause fluid flow along the at least one second (external) flow path 20 and/or the at least one first (internal) flow path 18, as described in greater detail below.

In other embodiments, the proximal end 57 of the positioning portion 53 may be spaced apart from the intermediate portion 60 by a distance less than, or equal to, a longitudinal length between the distal end 106 of the cannula shaft 14 and the instrument seal 110 of the cannula 102. This can mean that neither the positioning portion 53 or the intermediate portion 60 abut the cannula shaft 14 as the accessory 50 is slid through the shaft 14. In such instances, fluid can flow along the at least one first flow path 18 and/or the at least one second flow path 20.

Figure 3:
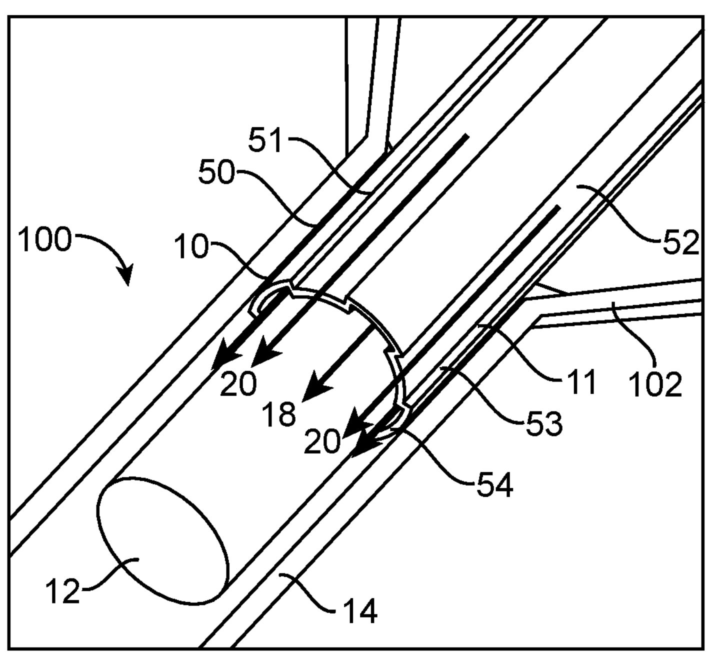
FIG. 3 is a detailed, perspective view of the accessory shown in FIG. 2, illustrated in use.
Figure 4:
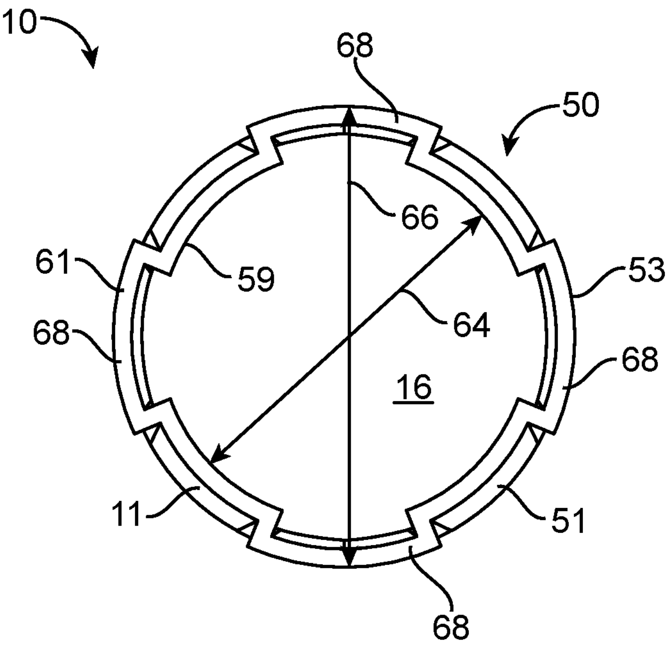
FIG. 4 is an end view of the accessory shown in FIG. 2.

FIGS. 3 and 4 show an embodiment of the positioning portion 53 of the accessory 50 in detail. Best shown in FIG. 4, the positioning portion 53 has a first, or inner, positioning portion 59. The first or inner positioning portion 59 defines an internal diameter 64 configured to position the body 51 relative to the instrument 12, such as being configured to arrange the positioning portion 53 on, or close to, at least two locations of the instrument 12 to allow defining the at least one first flow path 18 between the body 51 and the instrument 12. The inner positioning portion 59 may be dimensioned to abut, or be arranged immediately adjacent, the instrument 12 at the at least two locations to form the at least one first flow path 18.

The positioning portion 53 also has a second, or outer, positioning portion 61. The second or outer positioning portion 61 defines an external diameter 66 configured to position the body 51 relative to the cannula shaft 14, such as being configured to arrange the positioning portion 53 to contact, or be close to, at least two locations to allow defining the at least one second flow path 20 between the body 51 and the shaft 14. The outer positioning portion 53 may be dimensioned to abut, or be arranged immediately adjacent, the shaft 14 to form the at least one second flow path 20.

In this embodiment, each of the inner positioning portion 59 and the outer positioning portion 61 extend axially along the same portion of the body 51 to be aligned with each other. In other embodiments (not illustrated), the inner positioning portion 59 and the outer positioning portion 61 are arranged to be axially offset from each other to only partially overlap, or to be axially spaced from one another.

FIG. 4 illustrates the body 51 defines the open distal end 54 and the passage 16 dimensioned to receive the surgical instrument. The body 51 has an external region defining the outer positioning portion 61 configured to be coincident to an outer notional, or virtual, circle in at least one location. In this embodiment 50, the outer positioning portion 61 is coincident with the outer notional circle to extend along four portions of the circle. The body 51 also has an internal region defining an inner positioning portion 59 configured to be coincident to an inner notional, or virtual, circle in at least one location. In this embodiment 50, the inner positioning portion 59 is coincident with the inner notional circle to extend along four portions of the circle. It will be appreciated that in other embodiments, the outer positioning portion 61 and the inner positioning portion 59 may be tangential to the respective notional circle at one or more locations, such as the positioning portion 73 shown in FIG. 6 and discussed below.

In this embodiment 50, the positioning portion 53 is shaped to concentrically position the instrument 12 and the shaft 14 by contacting, or being arranged immediately adjacent, four locations, being two pairs of opposed locations, to allow defining four first flow paths 18 and four second flow paths 20. It will be appreciated that the positioning portion 53 may be shaped to position the instrument 12 and/or the cannula shaft 14 in more, or fewer, locations to allow defining more, or less, flow paths 18, 20. For example, in some embodiments (not illustrated), the distal portion 52 defines an oval or elliptical-shaped section having a maximum external width dimensioned to contact, or be adjacent, the cannula shaft 14 at two opposed locations, and a minimum internal height dimensioned to contact, or be adjacent, the instrument 12 at two opposed locations. In other embodiments (not illustrated), the distal portion 52 defines a triangular or square section shaped to closely bound the instrument 12 and snugly fit within the cannula shaft 14 such that the distal portion contacts, or is adjacent, three, or four, locations. In yet other embodiments (not illustrated), the positioning portion 53 is shaped to wrap at least partly about the instrument 12 to abut the instrument 12 in a single location. In such embodiments, the positioning portion 53 may be configured to partly wrap about the instrument 12 to abut the instrument 12 in a single location, with some embodiments configured to wrap around 30-70% around the circumference of the instrument 12, and other embodiments wrapping around equal to or greater than 50% of the circumference.

The distal portion 52 may define part of the bore 16 to extend at least partially along the instrument 12 in at least two locations to define at least two first flow paths 18. The distal portion 52 may additionally define an external region shaped to extend at least partially along the cannula shaft 14 in at least two locations to define at least two second flow paths 20. Best shown in FIG. 3, in the illustrated embodiment 50, the positioning portion 53 is shaped to extend partially along the instrument 12 to define four separate first flow paths 18, and shaped to extend partially along the cannula shaft 14 to define four separate second flow paths 20.

Returning to FIG. 4, at least some of the distal portion 52 defines a cross-sectional profile having an array of hollow projections 68 extending radially outwards from the bore 16. Each projection 68 may be dimensioned to abut, or be arranged immediately adjacent, the inner surface of the cannula shaft 14. In this embodiment 50, the projections 68 are configured as opposed pairs of hollow lobes arranged to position the body 51 at opposed sides of the cannula shaft 14. In the illustrated embodiment, each lobe defines an outer surface for positioning the body 51 in the inner surface of the shaft 14. The lobe outer surface may be curved. Between each lobe is an inner surface for positioning the body 51 on the instrument 12. The inner surface may be curved. The lobes are arranged in an annular array to be evenly spaced about the bore 16. In other embodiments (not illustrated), it will be appreciated that the projections 68 may be arranged in a non-regular array and/or configured to define other shapes, such as corrugations, castellations, or the like.

The projections 68 are configured to arrange the instrument 12 and the accessory 50 substantially coaxially to the cannula shaft 14. This may allow fluid, such as gas received from the gas source 202, to flow along the second flow paths 20 and flow axially alongside the accessory 50, and/or through the bore 16, and along the first flow paths 18 to be concentric to the instrument 12, as indicated by the arrows illustrated in FIG. 3. In the illustrated embodiment 50, the projections 68 are further configured to slidingly engage the instrument 12 and the cannula shaft 14. In some embodiments, the projections 68 may frictionally engage at least one of the instrument 12 and the shaft 14 to inhibit relative axial and/or rotational movement.

Figure 5:
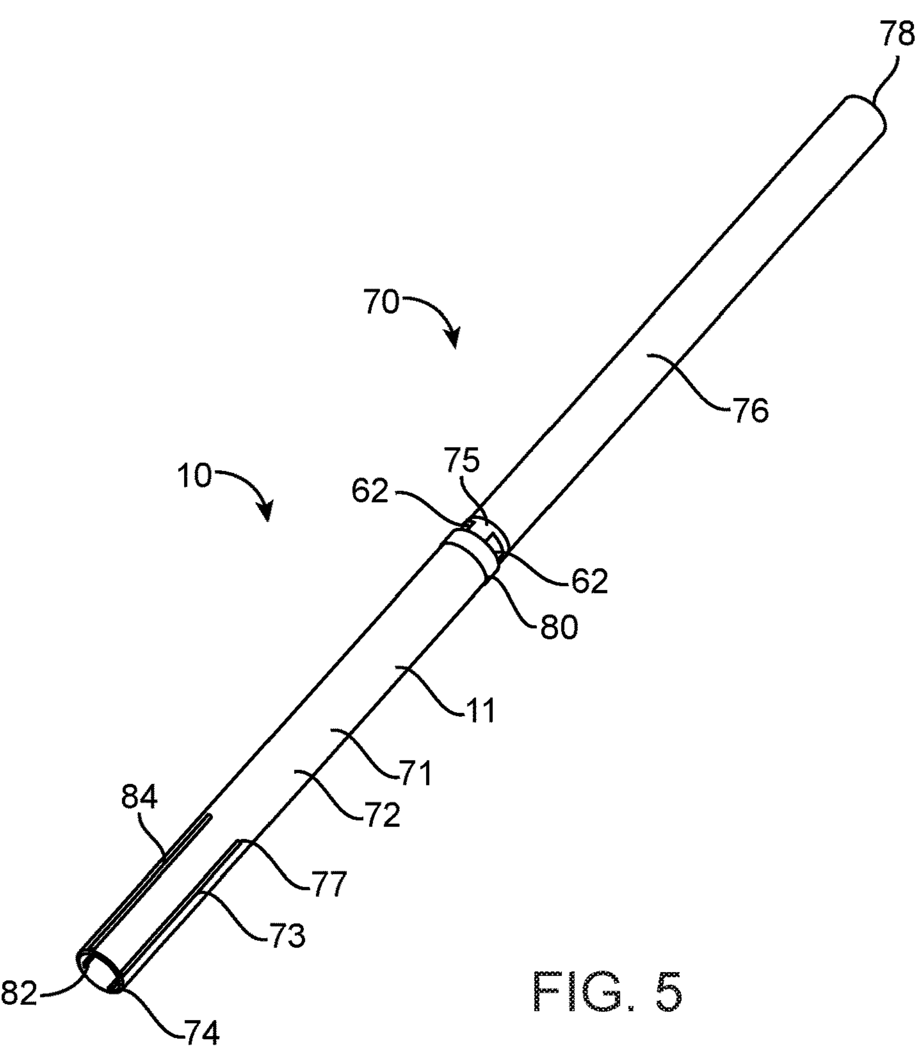
FIG. 5 is a perspective view of an alternative embodiment of the accessory shown in FIG. 2.
Figure 6:
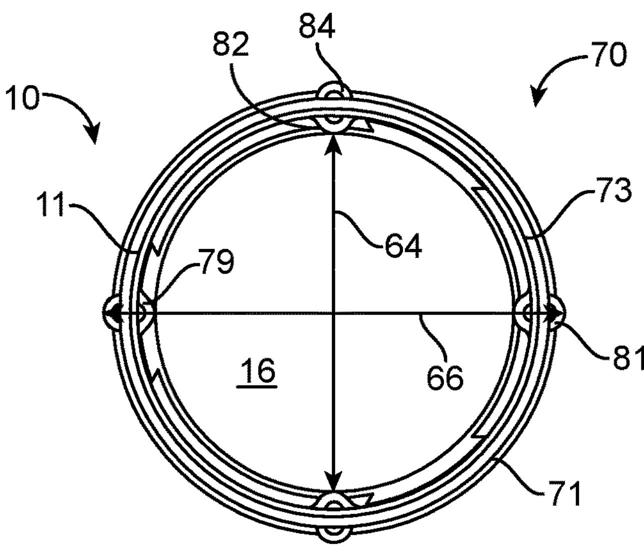
FIG. 6 is an end view of the accessory shown in FIG. 5.

FIGS. 5 and 6 illustrate a second embodiment of the accessory 70. This embodiment 70 shares features with the first illustrated embodiment 50, whereby common reference numerals indicate common features.

The second embodiment of the accessory 70 has a body 71 which includes a distal portion 72 defining an open distal end 74, a proximal portion 76 defining a proximal end 78, and an intermediate portion 80, or sealing portion, interposed between the distal portion 72 and the proximal portion 76 and configured to seal against the cannula shaft 14. In the illustrated embodiment 70, the portions 72, 76, 80 of the body 71 are formed to define a unitary body 71. The bore 16 is defined between the distal end 74 and the proximal end 78 such that the proximal end 78 is open to allow receiving the instrument 12 into the bore 16.

The distal portion 72 defines a positioning portion 73, being a structure shaped and dimensioned such that, in use, the structure positions the accessory 70 relative to the cannula shaft 14 and/or the instrument 12. The positioning portion 73 may be configured to abut at least one of the cannula shaft 14 and the instrument 12. The positioning portion 73 may be dimensioned to allow clearance between the shaft 14 and instrument 12. The clearance may be defined within a tolerance, for example, less than 0.5 mm. In some embodiments, the positioning portion 73 is configured for sliding engagement with the shaft 14 and/or instrument 12. In the illustrated embodiment 70, the positioning portion 73 defines a proximal end 77 spaced axially from the intermediate portion 80.

In some embodiments, the proximal end 77 of the positioning portion 73 may be spaced apart from the intermediate portion 80 by a distance less than, or equal to, a longitudinal length of the cannula shaft 14. In other embodiments, the proximal end 77 of the positioning portion 73 may be spaced apart from the intermediate portion 80 by a distance less than, or equal to, a longitudinal length between the distal end 106 of the cannula shaft 14 and the instrument seal 110 of the cannula 102.

Best shown in FIG. 6, the positioning portion 73 defines the internal diameter 64 within the bore 16, and defines the external diameter 66. The internal diameter 64 is defined by a first, or internal, positioning portion 79 having a plurality of internal projections, in the form of longitudinally extending internal ribs 82. The external diameter 66 is defined by a second, or external, positioning portion 81 having a plurality of external projections, in the form of longitudinally extending external ribs 84. Each rib 82, 84 is dimensioned to extend radially relative to the bore 16 and at least partially along the instrument 12 and the cannula shaft 14 to define the at least one first flow path 18 and the at least one second flow path 20.

The positioning portion 73 may be configured such that the internal ribs 82 are arranged to tangentially abut the instrument 12 or a notional circle spaced about the instrument 12 to allow clearance, and the external ribs 84 are arranged to tangentially abut the cannula shaft 14 or a notional circle spaced within the shaft 14 to allow clearance. In this embodiment 70, the ribs 82, 84 are arranged in opposed pairs evenly spaced about the bore 16 to allow positioning the body 71 at opposed locations of the instrument 12 and cannula shaft 14. It will be appreciated that the number and arrangement of internal and external projections defined by the distal portion 72 is exemplary and that the distal portion 72 may include more, or fewer, projections arranged in a regular or irregular array. In some embodiments (not illustrated), the internal and/or external projections define discontinuous structures, such as discrete bulges, domes, spikes, fingers, or the like, to allow positioning the accessory 70 relative to the instrument 12 and the cannula shaft 14.

Figure 7:
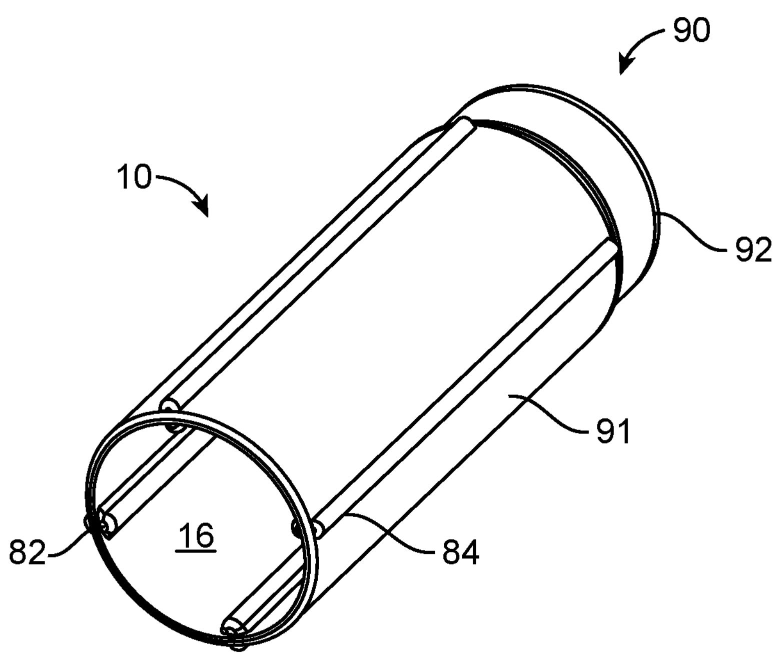
FIG. 7 is a perspective view of a further alternative embodiment of the accessory shown in FIG. 2.

FIG. 7 illustrates a further embodiment 90 of the accessory 10. This embodiment 90 shares features with the previously described embodiments 50, 70, whereby common reference numerals indicate common features. The embodiment 90 is effectively equivalent to the positioning portion 53, 73 configured as a separate component which is removably or permanently connectable to the distal portion 52, 72 or intermediate portion 60, 80 to form the body 51, 71.

In this embodiment 90, the positioning portion 53, 73 is configured as a first sleeve 90. The sleeve 90 includes a body 91 which defines a proximal end 92 configured for attachment to a second sleeve (not illustrated). The second sleeve may be a cylindrical tubular body configured to fit within the cannula shaft 14 and receive the instrument 12. In some embodiments (not illustrated), the second sleeve comprises at least the intermediate portion 60, 80 and proximal portion 56, 76 of the accessories 50, 70 described above. In other embodiments (not illustrated), the second sleeve comprises a distal portion 52, 72 in addition to the intermediate portion 60, 80 and proximal portion 56, 76. The sleeve 90, when attached to the second sleeve, functions in the same way to the positioning portion 53, 73 described above.

The sleeve 90 has one or more structures shaped and dimensioned such that in use, the structure(s) position the accessory 90 relative to the cannula shaft 14 and/or the instrument. Similar to the positioning portion 53, 73 described above, the structure(s) may be configured to position the body 91 relative to at least one of the cannula shaft 14 and the instrument 12.

In the embodiment 90 shown in FIG. 7, the sleeve 90 has a first, or inner, positioning portion 82. The first or inner positioning portion 82 defines an internal diameter configured to position the body 91 on the instrument 12 in at least two locations. The sleeve 90 also has a second, or outer, positioning portion 84. The second, or outer positioning portion defines an external diameter configured to position the body 91 in the cannula shaft 14 in at least two locations.

In the embodiment shown, the first/inner positioning portion 82 and second/outer positioning portion 84 are in the form of ribs 82, 84 to allow positioning the sleeve 90 relative to the instrument 12 and/or the cannula shaft 14. In other embodiments (not shown), the inner and/or external positioning portions 82, 84 can be provided as other structures, such as one or more of discrete bulges, domes, spikes, fingers or lobes, such as described above.

The sleeve 90 is provided as a component that removably or permanently attaches to the second sleeve. This allows the same second sleeve to be used with a range of differently configured sleeves 90, such as having different inner and/or outer positioning portion geometries suited to position the sleeve 90 relative to different types and/or sizes of instruments and/or cannulas.

Figure 8:
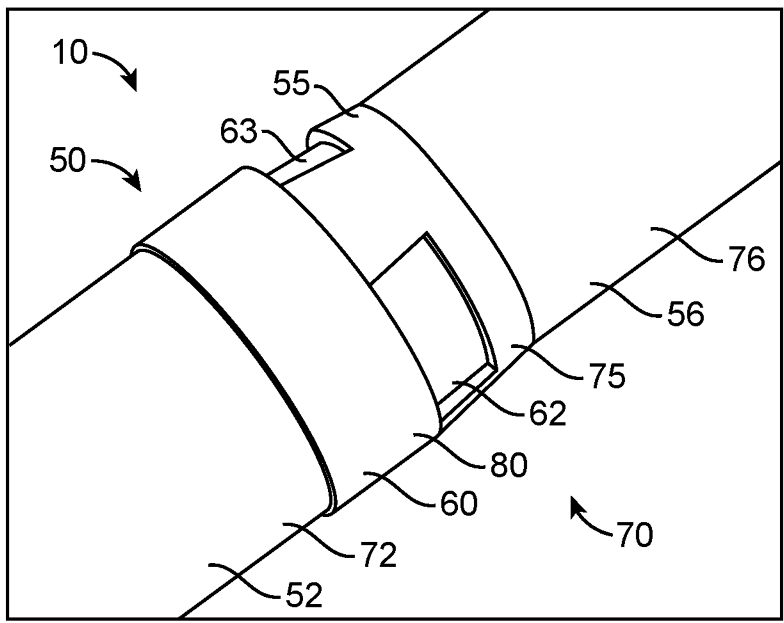
FIG. 8 is a detailed perspective view of part of the accessory shown in FIG. 2.

FIG. 8 illustrates the intermediate portion 60, 80 of the above-described embodiments 50, 70 in detail. As described above, the intermediate portion 60, 80 is configured to seal against the cannula shaft 14. The intermediate portion 60, 80 can seal against the cannula shaft 14 such as by frictional engagement and/or by carrying one or more compressible seals, such as O-rings.

The proximal portion 56, 76 defines the array of apertures 62 arranged to allow access to the bore 16. In the illustrated embodiments 50, 70, the proximal portion 56, 76 defines a tapered region 55, 75 extending away from the intermediate portion 60, 80. The tapered region 55, 75 defines a maximum diameter at its distal end and minimum diameter at its proximal end to gradually transition between a diameter defined by the intermediate portion 60, 80 and a diameter defined by the proximal portion 56, 76.

In the illustrated embodiments, 50, 70, each aperture 62 is defined in the tapered region 55, 75. It will be appreciated that, in other embodiments (not illustrated), the tapered region 55, 75 may define an alternative structure, such as being stepped, or be absent and/or the apertures 62 be spaced apart from the intermediate portion 60, 80 along the proximal portion 56, 76. For example, in some embodiments (not illustrated), the tapered region 55,75 is alternatively configured as a re-entrant region which transitions from the maximum diameter to the minimum diameter via a re-entrant structure.

In the illustrated embodiments 50, 70, the apertures 62 are associated with one or more one-way valves 63, or seals, configured to restrict fluid flow to a single direction through the apertures 62, being towards the bore 16. The arrangement of the valves 63 in this way allows directing fluid travelling between the accessory 50, 70 and the cannula 102, through the apertures 62, and into the bore 16 to travel between the accessory 50, 70 and the instrument 12. In the illustrated embodiments 50, 70, a complementary plurality of valves 63 to the plurality of apertures 62 are arranged within the bore 16, such that each aperture 62 is associated with, and covered by, one of the valves 63. It will be appreciated that in some embodiments (not illustrated), a single valve may be arranged across all of the apertures 62. In yet other embodiments (not illustrated), the apertures 62 are not associated with a valve or seal and allow fluid to flow freely through the apertures 62.

In the illustrated embodiments 50, 70, the proximal portion 56, 76 is configured to seal against the instrument 12 at a location spaced proximally from the apertures 62. In some embodiments, the proximal portion 56, 76 is dimensioned to frictionally engage the instrument 12. Additionally or alternatively, the proximal portion 56, 76 carries a resiliently deformable seal arranged to be deformed by, and seal against, the instrument 12. In further embodiments (not illustrated), the proximal portion 56, 76 includes a sealing mechanism, such as a cam-lock actuated mechanism, to cause sealing against the instrument 12. Additionally or alternatively, the proximal portion 56, 76 includes a rotation mechanism operable to rotationally position, and optionally lock, the instrument 12 relative to the accessory 50, 70.

FIGS. 9 to 17 illustrate the system 200 during various stages of use, for example, during a surgical or other medical procedure. In practice, the gas source 202, or another fluid source, is coupled to the gas inlet port 104 of the cannula 102. For simplicity, the gas source 202 is hidden in these figures.

The accessory 50 may be mounted over the instrument 12 such that a distal end of the instrument 12 is at least flush with the distal end 54 of the accessory 50. Alternatively, as shown in FIGS. 9 to 17, the accessory 50 is mountable over the instrument 12 such that the distal end of the instrument 12 protrudes from the distal end 54 of the accessory 50. The accessory 50 is configured to be arranged relative to the instrument 12 such that the instrument 12 protrudes from the distal end 54 of the accessory 50 by a predetermined distance. In some embodiments, the accessory 50 may be arranged such that the distal end of the instrument 12 protrudes outwardly from the distal end 54 of the accessory 50 by about 0 to 25 mm, and typically about or 10 to 20 mm. For example, when the instrument 12 is a scope, the accessory 50 may be arranged such that the scope lens is positioned out of the distal end 54 of the accessory 50 within a range of around 10-20 mm past the distal open end 54. In some embodiments, the accessory 50 is configured to retain the instrument 12 in position, such as by operating a locking means associated with the accessory 50.

In some embodiments, the accessory 50 may be mounted over the instrument 12 such that a distal end of the instrument 12 is, in use, located inside the bore 16. The distal end of the instrument 12 may be located in the bore 16 a distance inwards from the distal end 54 of the accessory 50. For example, when the instrument 12 is in the form of a scope, the scope lens can be located inside the bore 16. When in such a configuration, the distal end 54 of the accessory 50 will, in use, extend further into the body cavity than the distal end of the instrument 12.

Figure 9:
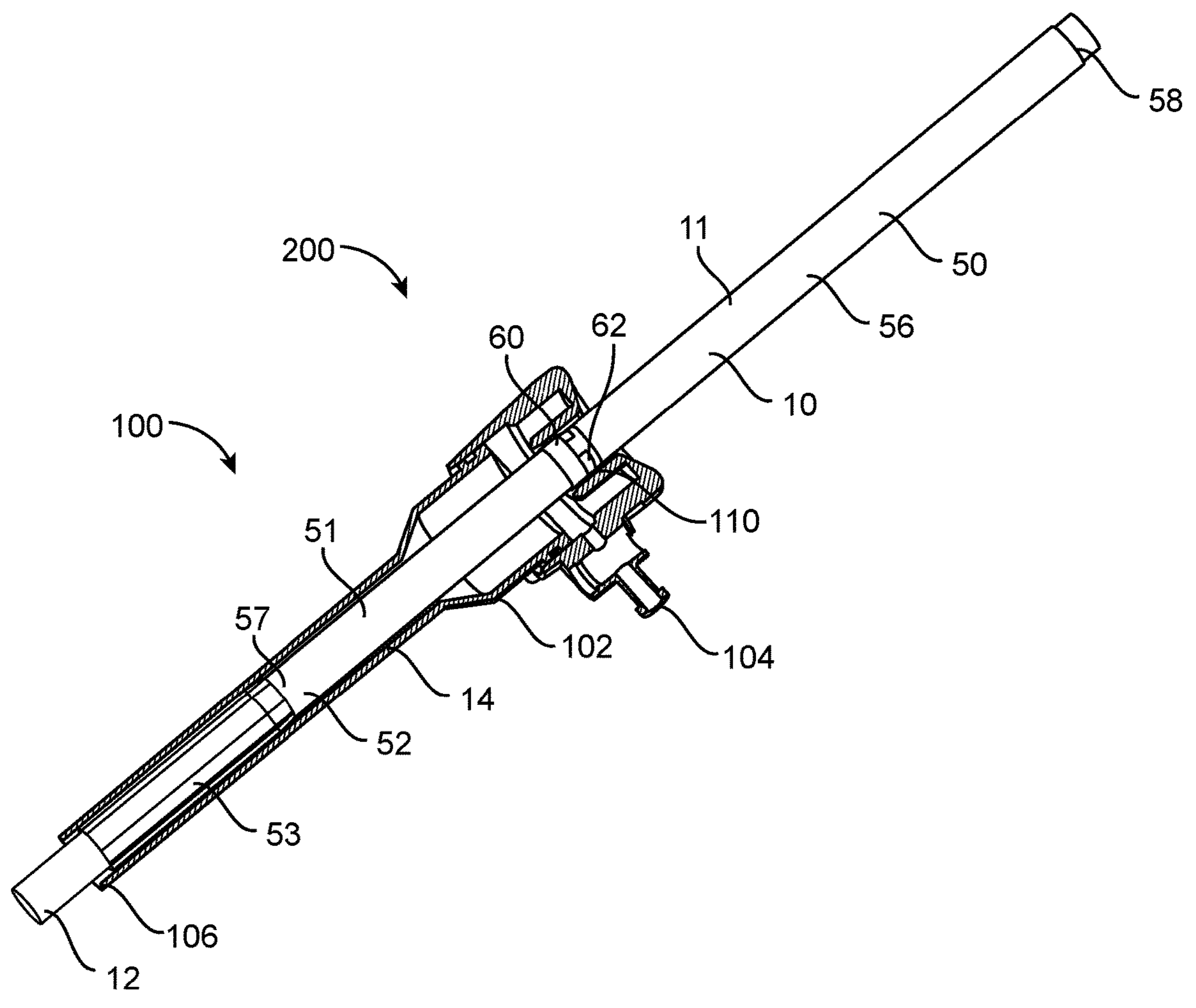
FIG. 9 is a partial section, perspective view of the assembly shown in FIG. 1, illustrating a first in use configuration.
Figure 10:
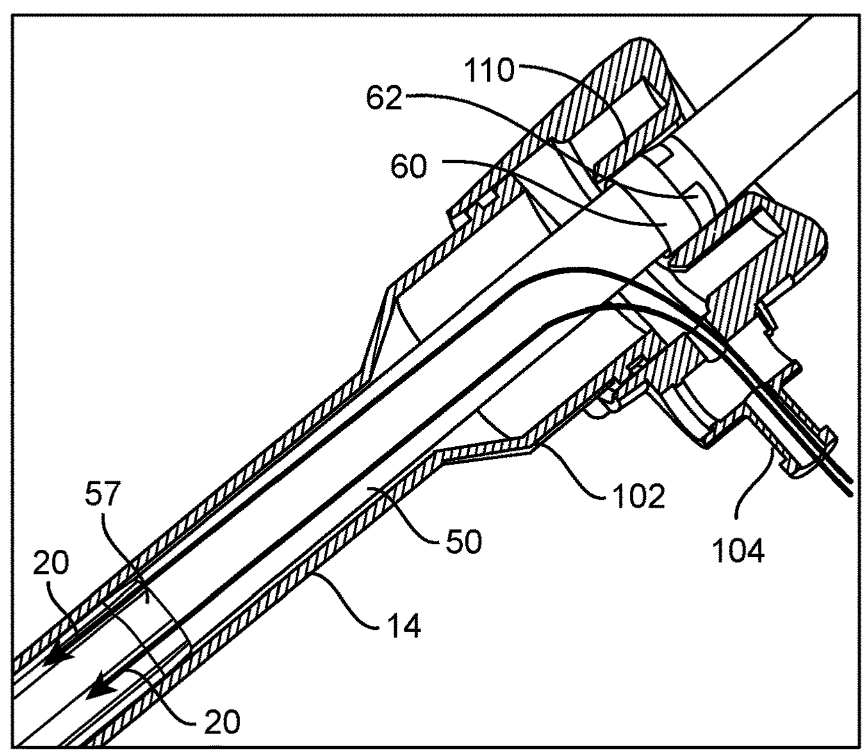
FIGS. 10 and 11 are detailed perspective views of parts of the assembly shown in FIG. 9, during use.
Figure 11:
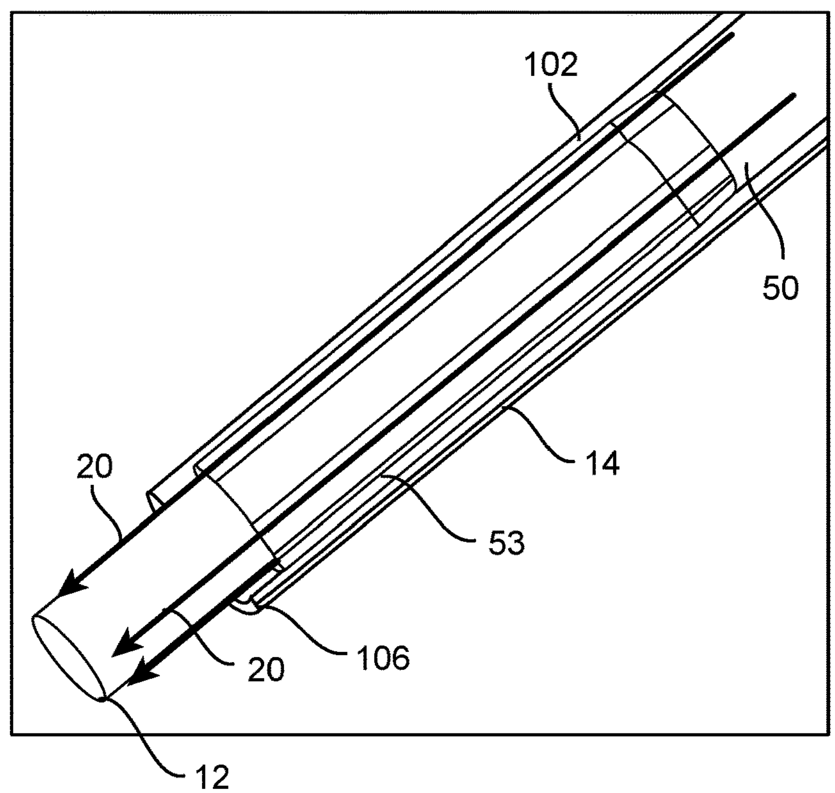
Figure 12:
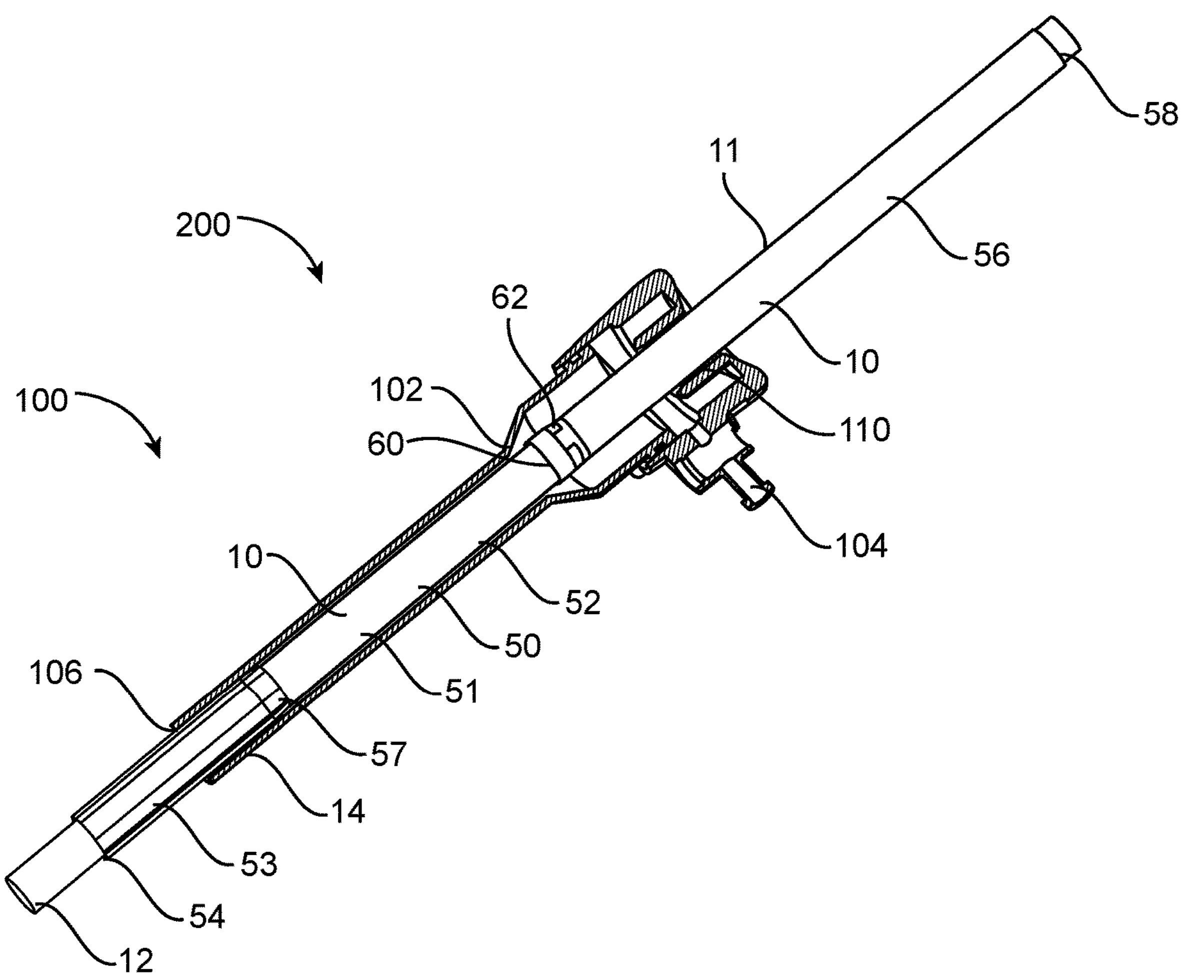
FIG. 12 is a partial section, perspective view of the assembly shown in FIG. 1, illustrating a second in use configuration.
Figure 13:
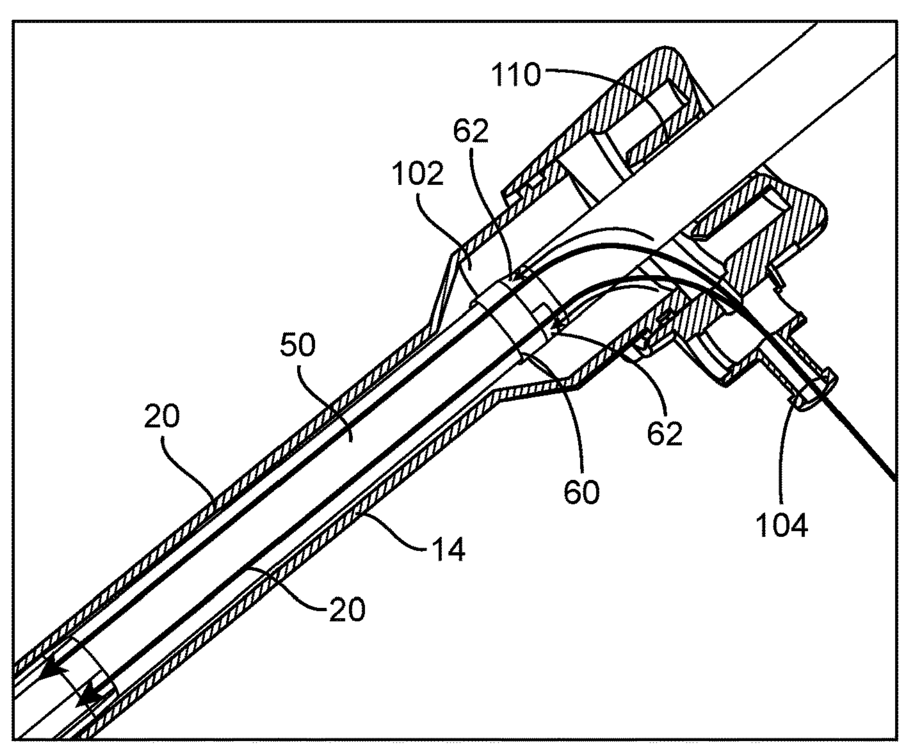
FIGS. 13 and 14 are detailed perspective views of parts of the assembly shown in FIG. 12, during use.
Figure 14:
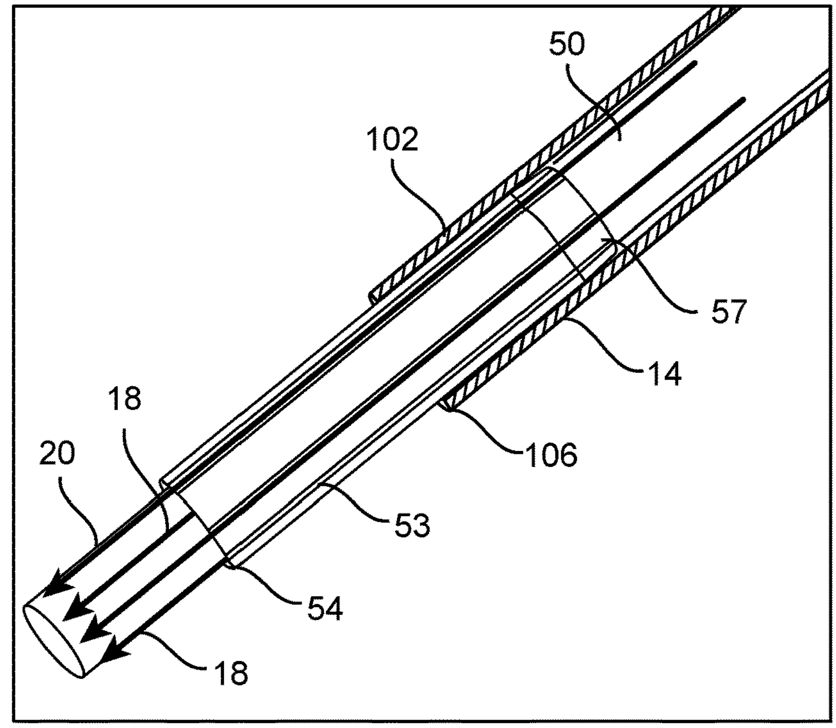
Figure 15:
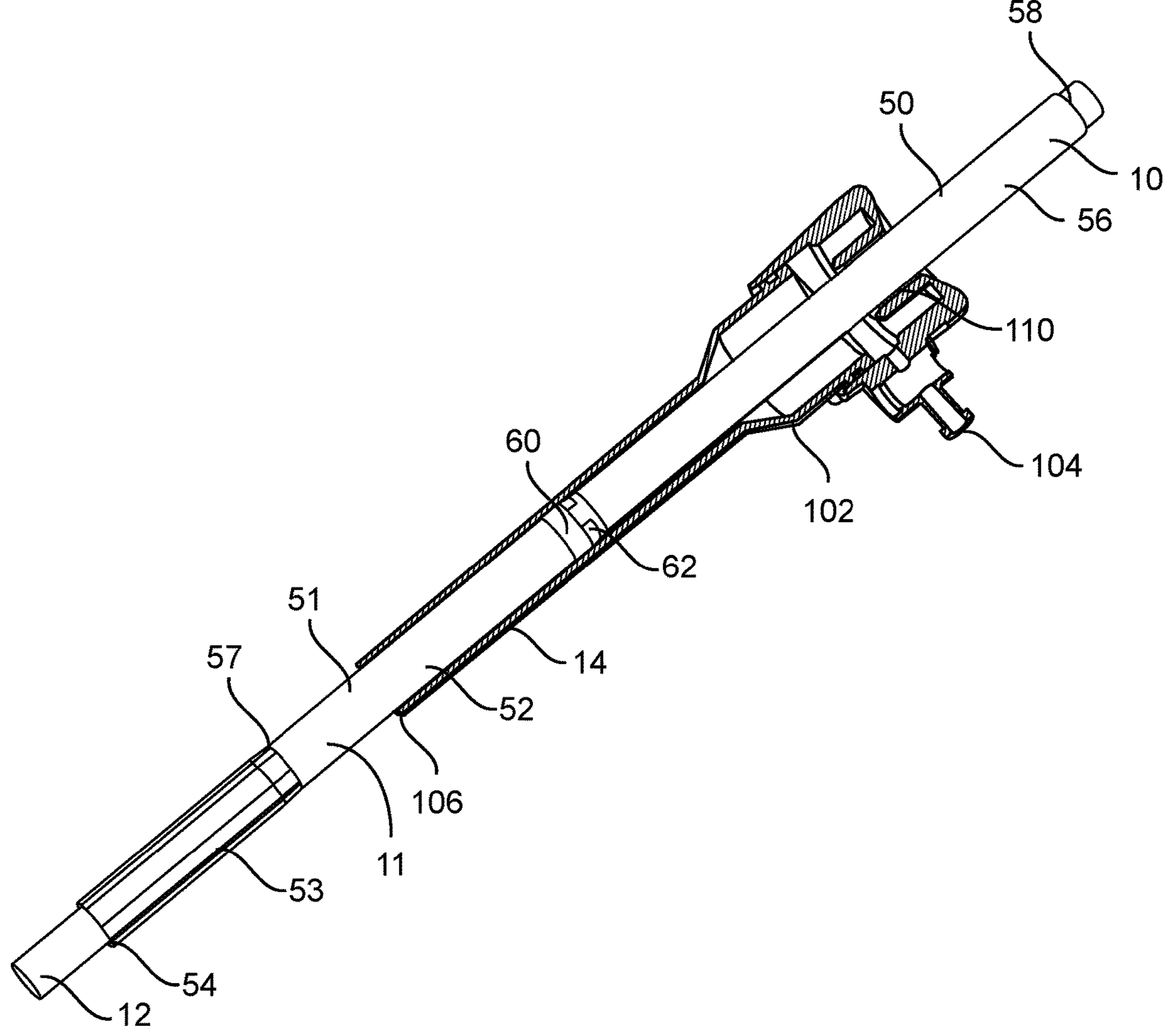
FIG. 15 is a partial section, perspective view of the assembly shown in FIG. 1, illustrating a third in use configuration.
Figure 16:
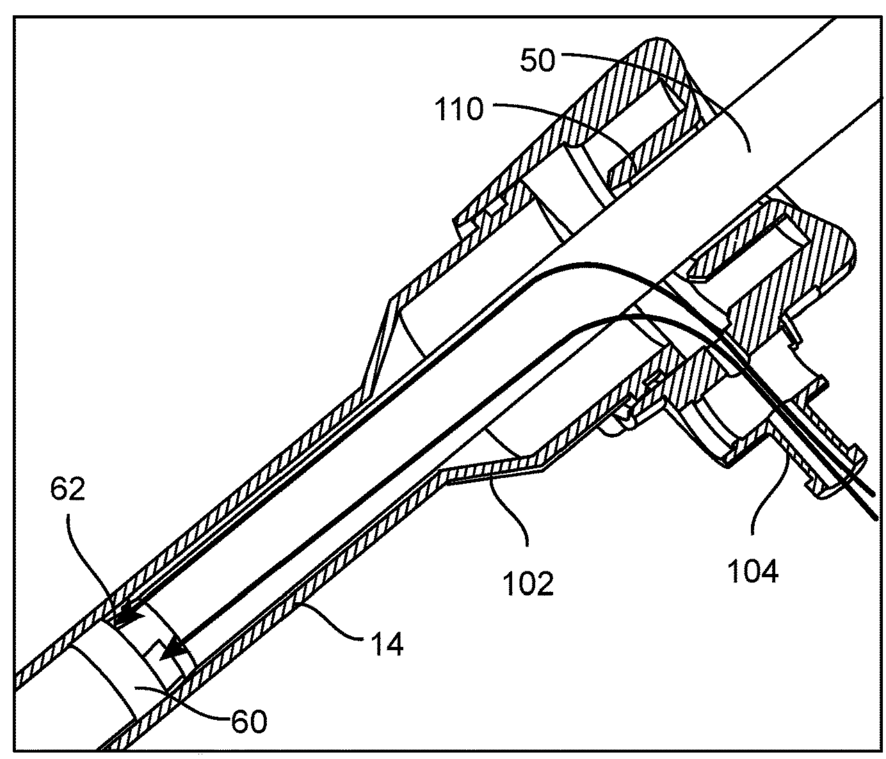
FIGS. 16 and 17 are detailed perspective views of parts of the assembly shown in FIG. 15, during use.
Figure 17:
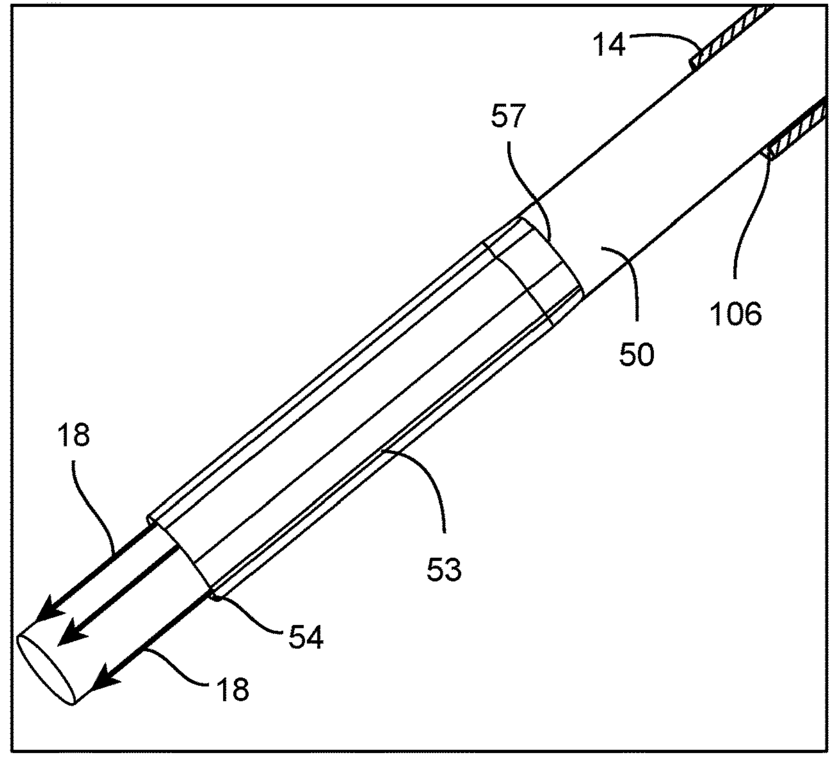

FIGS. 9 to 11 illustrate the assembly 100 in a first configuration to cause gas to flow through the cannula shaft 14 via the at least one second flow path 20 only. FIGS. 12 to 14 illustrate the assembly 100 in a second configuration to cause gas to flow through the cannula shaft 14 via the at least one first flow path 18 and the at least one second flow path 20. FIGS. 15 to 17 illustrate the assembly 100 in a third configuration to cause gas to flow through the cannula shaft 14 via the at least one first flow path 18 only.

In each of the configurations, the assembly 100 includes the instrument 12 arranged within the accessory 50, and the accessory 50 arranged within the cannula shaft 14. Relative movement of the accessory 50 and cannula 102 causes transitioning between the configurations. The accessory 50 is arranged to allow gas, or other fluid, to flow axially along the cannula shaft 14 to bypass the instrument 12, or bypass the instrument 12 and the accessory 50. Where the instrument 12 is configured as a scope having a lens to allow obtaining an image, in each configuration the accessory 50 is arranged to cause gas to flow past the lens.

Referring to FIGS. 9 to 11, in the first configuration, the accessory 50 is arranged at a first insertion position relative to the cannula shaft 14 so that the apertures 62 are arranged to be spaced from the housing seal 110 in the proximal direction to be operatively outside of the cannula 102 or, as shown in FIG. 9, arranged at the housing seal 110. In this first configuration, the housing seal 110 seals against the accessory 50. This arrangement means that gas which is conveyed through the gas inlet port 104 and into the cannula 102 is caused to flow axially through the cannula shaft 14 between the cannula 102 and the accessory 50. This causes the gas to flow along the second flow paths 20 defined between the accessory 50 and the cannula shaft 14, to pass the accessory 50 and exit from the distal end 106 of the cannula shaft 14. The gas exits the cannula shaft 14 to flow concentrically to, and past the distal end of, the instrument 12.

Gas flow is delineated by single headed arrows in FIGS. 10 and 11. In this configuration, gas conveyed into the cannula 102 is inhibited from entering the apertures 62 of the accessory 50. The apertures 62 are axially spaced apart from the housing seal 110 meaning that the seal 110 substantially prevents the gas from passing into any aperture 62.

Referring to FIGS. 12 to 14, in the second configuration, the accessory 50 is arranged at a second insertion position relative to the cannula shaft 14 so that the apertures 62 are arranged within the cannula 102 spaced between the housing seal 110 and the shaft 14. This arrangement means that gas which is conveyed through the gas inlet port 104 and into the cannula 102 may flow into the apertures 62 and along the bore 16 concurrently with flowing along the outside of the accessory 50. This may allow gas to flow axially through the cannula shaft 14 along the first flow paths 18 defined between the accessory 50 and the instrument 12, and to exit from the distal end 54 of the accessory 50, concurrently with flowing axially through the cannula shaft 14 along the second flow paths 20 defined between the accessory 50 and the cannula shaft 14, to pass the accessory 50 and exit from the distal end 106 of the shaft 14. The gas exits the accessory 50 and the cannula shaft 14 to flow concentrically to, and past the end of, the instrument 12. Gas flow is delineated by single headed arrows in FIGS. 13 and 14.

Referring to FIGS. 15 to 17, in the third configuration, the accessory 50 is arranged at a third insertion position relative to the cannula shaft 14 so that the intermediate portion 60 is arranged within, and sealing against, the cannula shaft 14. This arrangement means that gas which is conveyed through the gas inlet port 104 and into the cannula 102 is caused to flow into the apertures 62 and flow axially along the bore 16 of the accessory 50 while the intermediate portion 60 inhibits gas flowing axially past the intermediate portion 60 and along the outside of the accessory 50. This means that the gas flows axially through the cannula shaft 14 along the first flow paths 18 defined between the accessory 50 and the instrument 12 to exit from the distal end 54 of the accessory 50. The gas exits the accessory 50 to flow concentrically to, and past the end of, the instrument 12.

Gas flow is delineated by single headed arrows in FIGS. 16 and 17. This configuration can usefully extend the insertion depth at which gas flow can be directed relative to the instrument 12, for example, within a body cavity.

Where the instrument 12 is a scope having a viewing portion, such as a lens at its distal end, each configuration as described above may cause the gas to flow relative to the lens. This can mitigate or avoid collection of fluid droplets on the lens, and/or assist in removing fluid and/or other matter from the lens, and/or displace fluid and/or other matter positioned in front of the lens, such as caused by condensation and/or the lens being positioned against or adjacent body fluids, tissue or other particles, such as smoke.

The accessory 10 may be used to deliver gases to a body cavity (not illustrated). In this scenario, the cannula 102 is inserted into the site, such as through an incision made in, or natural orifice defined in, the body. Use of the accessory 10 may involve inserting the surgical instrument 12 into the accessory 10, in the form of a sheath 10, to define at least one first flow path 18 between the sheath 10 and the instrument 12, inserting the sheath 10 into the cannula shaft 14 to define at least one second flow path 20 between the sheath 10 and the cannula shaft 14, and conveying gases through one or more of the at least one first flow path 18 and the at least one second flow path 20 to exit into the surgical site.

Inserting the instrument 12 into the accessory 10 arranges the instrument 12 within the bore 16 of the accessory 10. This may cause the instrument 12 to slide along a structure within the bore 16 to position the instrument 12 relative to the accessory 10. In some embodiments, this causes the instrument 12 to urge against a seal structure to form a seal between the accessory 10 and the instrument. Additionally or alternatively, this may cause the instrument 12 to be placed against, or engage with, a retention structure configured to retain the instrument 12 within the bore 16, such as by inhibiting relative axial and/or rotational movement between the instrument 12 and the accessory 10.

In some embodiments, a proximal end of the accessory 10 may abut a proximal portion of the instrument 12. For example, when the instrument 12 is a scope, the proximal end of the accessory 10 may be configured to abut a ledge or other similar structure at the proximal end of the scope.

The instrument 12 is inserted into the bore 16 of the accessory 10 and positioned therein such that the distal end of the instrument 12 is flush with, or extends beyond, the distal end of the accessory 10. The distal end of the instrument 12 may extend a distance within the range of 0-25 mm out from the distal end of the accessory 10.

Inserting the sheath 10 into the cannula shaft 14 typically involves inserting the sheath 10 a defined distance into the cannula shaft 14. The defined distance, or insertion depth, affects the path that the gas will flow axially through the cannula shaft 14 and relative to the sheath 10 and instrument 12. For example, inserting the sheath 10 a first distance causes the gases to flow through the at least one second flow path 20. Inserting the sheath a second distance, being greater than the first distance, causes the gases to flow through the at least one first flow path 18. Also, inserting the sheath a third distance, being greater than the first distance and less than the second distance, causes the gases to flow through the at least one second flow path 20 and the at least one first flow path 18.

The disclosed accessory 10 allows positioning the instrument 12 relative to the accessory 10, and positioning the accessory 10 relative to the cannula shaft 14, to define the at least one first flow path 18 and the at least one second flow path 20. Defining the flow paths in this way allows fluid, typically being gas, to flow axially through the cannula shaft 14 between the outside of the accessory 10 and the cannula shaft 14, and/or between the inside of the accessory 10, being the bore 16, and the instrument 12. This can direct fluid flow out of the cannula shaft 14 and/or bore 16 of the accessory 10 and relative to an end of the instrument 12. Fluid can be directed out of the cannula shaft 14 and/or the bore 16 of the accessory 10 substantially concentrically to the end of the instrument 12. Where the instrument 12 is a scope having an end including a lens or viewing portion, this can direct the fluid flow relative to the lens or viewing portion, which can inhibit fluid or debris collecting on the lens and/or remove fluid or debris from the lens.

The accessory 10 is positionable relative to the cannula shaft 14 such that the accessory 10 extends from the shaft 14. This allows the distal end of the accessory 10 to be spaced away from the distal end 106 of the shaft 14. This arrangement can effectively extend the insertion depth at which fluid can be directed out of the cannula shaft 14 and relative to the instrument 12. In other words, the accessory 10 can allow delivery of directed fluid flow substantially concentric to the end of the instrument 12, e.g. scope lens, at an insertion depth beyond the distal end 106 of the cannula. This can be useful to enhance vision through a scope at insertion depths greater than the length of the cannula shaft 14, including by clearing regions containing stagnant smoke or the like and/or inhibiting collection of fluid and/or debris on the scope lens.

The accessory 10 allows directing fluid flow relative to the instrument 12 without requiring any adaptation of the cannula 102, or significant amendment to surgical practices. For example, the accessory 10 is configurable to retro-fit to a conventional cannula and receive a conventional scope. The accessory 10 is configured to receive and/or direct gas conveyed into the cannula 102 through the gas inlet port 104 to exit from the cannula shaft 14 and/or accessory 10. In other words, the accessory 10 can use existing gas flow in an insufflation cannula. This allows the accessory 10 to be used with a conventional cannula 102 and does not require cannula modification, such as bifurcation of an insufflation line.

The accessory 10 is configurable to receive a range of different instruments and direct fluid flow relative to the instrument 12, including angled and zero-angle scopes. The accessory 10 is additionally configurable to receive and operate with a range of different sized instruments, including instruments having different lengths and/or diameters.

The accessory 10 can be readily mounted over an instrument 12 without requiring precise or particular orientation with respect to the instrument 12. Once mounted on the instrument 12, the accessory 10 can be used to mitigate vision problems for an operator of the instrument 12 without requiring modification of workflow.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

What is claimed is:

1. An accessory for arranging a surgical instrument within a cannula shaft, the accessory including:

an accessory body defining:

a bore configured to receive the surgical instrument such that arranging the surgical instrument within the bore defines a first flow path between the accessory body and the surgical instrument, at least one aperture arranged to allow fluid flow into the bore and along the first flow path when the at least one aperture is positioned at a first location relative to the cannula shaft, a plurality of internal projections extending into the bore and configured to position the accessory body relative to the surgical instrument, and a plurality of external projections extending away from the bore and configured to position the accessory body relative to the cannula shaft, the accessory body comprising:

a proximal portion defining an open proximal end, a distal portion defining an open distal end, the bore defined between the open proximal end and the open distal end, an intermediate portion interposed between the proximal portion and the distal portion and configured to seal against the cannula shaft, the accessory body further defining a tapered region extending away from the intermediate portion, the at least one aperture defined in the tapered region, the accessory body configured to be received within the cannula shaft such that arranging the accessory body within the cannula shaft so the at least one aperture is positioned at a second location relative to the cannula shaft defines a second flow path between the accessory body and the cannula shaft, the accessory body configured to allow fluid flow into the cannula shaft and towards a distal end of the surgical instrument via one or more of the first flow path and the second flow path.

2. The accessory of claim 1, wherein the internal projections define an internal profile configured to position the accessory body on, or close to, the surgical instrument in at least two locations of the internal profile, and the external projections define an external profile configured to position the accessory body in the cannula shaft in at least two locations of the external profile.

3. The accessory of claim 2, wherein the internal and external projections are shaped to tangentially abut at least one of the surgical instrument in the at least two locations of the internal profile and the cannula shaft in the at least two locations of the external profile.

4. The accessory of claim 1, wherein the internal projections are shaped to extend at least partially along the surgical instrument in at least two locations to define the first flow path, and the external projections are shaped to extend at least partially along the cannula shaft in at least two locations to define the second flow path.

5. The accessory of claim 1, wherein at least one of the internal projections and the external projections are arranged in an annular array and evenly spaced about the bore.

6. The accessory of claim 1, wherein the internal projections are at least partially arranged in one or more opposed pairs to position the accessory body at opposed sides of the surgical instrument.

7. The accessory of claim 1, wherein the external projections are at least partially arranged in one or more opposed pairs to position the accessory body at opposed sides of the cannula shaft.

8. The accessory of claim 1, wherein one or more of the internal or external projections are longitudinally extending ribs.

9. The accessory of claim 1, wherein the accessory body is shaped to position at least one of: the surgical instrument coaxially to the bore; the surgical instrument coaxially to the cannula shaft; and the bore coaxially to the cannula shaft.

10. The accessory of claim 1, wherein the at least one aperture is adjacent the intermediate portion.

11. The accessory of claim 1, wherein the at least one aperture is spaced proximally to the intermediate portion.

12. The accessory of claim 1, wherein at least one one-way valve is arranged in the bore to control fluid flow through the at least one aperture.

13. The accessory of claim 1, wherein the accessory body is configured to seal against the surgical instrument at a location spaced proximally from the at least one aperture.

14. The accessory of claim 1, wherein the intermediate portion carries a resiliently deformable first seal configured to seal against the cannula shaft.

15. A method for delivering gases to a surgical site, the method including:

inserting a surgical instrument into a bore defined in a body of a sheath to define a first flow path between the body of the sheath and the surgical instrument;

the body of the sheath further defining:

at least one aperture arranged to allow fluid flow into the bore and along the first flow path when the at least one aperture is positioned at a first location relative to a cannula shaft, a plurality of internal projections extending into the bore and configured to position the body of the sheath relative to the surgical instrument, and a plurality of external projections extending away from the bore and configured to position the body of the sheath relative to the cannula shaft, the body of the sheath comprising:

a proximal portion comprising an open proximal end, a distal portion comprising an open distal end, the bore defined between the open proximal end and the open distal end, an intermediate portion interposed between the proximal portion and the distal portion and configured to seal against the cannula shaft, and the body of the sheath further defining a tapered region extending away from the intermediate portion, the at least one aperture defined in the tapered region, and inserting the sheath into the cannula shaft such that the at least one aperture is positioned at a second location relative to the cannula shaft to define a second flow path between the body of the sheath and the cannula shaft; and conveying gases through one or more of the first flow path and the second flow path to exit into the surgical site.

16. A sheath for a surgical instrument, the sheath including:

a body defining:

a bore configured to receive the surgical instrument such that arranging the surgical instrument within the bore defines a first flow path between the body and the surgical instrument, at least one aperture arranged to allow fluid flow into the bore and along the first flow path when the at least one aperture is positioned at a first location relative to a cannula shaft, a plurality of internal projections extending into the bore and configured to position the body relative to the surgical instrument, and a plurality of external projections extending away from the bore and configured to position the body relative to the cannula shaft;

the body comprising:

a proximal portion comprising an open proximal end, a distal portion comprising an open distal end, the bore defined between the open proximal end and the open distal end, an intermediate portion interposed between the proximal portion and the distal portion and configured to seal against the cannula shaft, the body further defining a tapered region extending away from the intermediate portion, the at least one aperture defined in the tapered region, and wherein the internal projections are configured to direct fluid flow axially through the bore along the first flow path to pass the surgical instrument arranged within the bore, and the external projections are configured to direct fluid flow axially adjacent the sheath through a second flow path when the at least one aperture is positioned at a second location relative to the cannula shaft to pass the sheath and the surgical instrument arranged within the bore.

* * * * *